United States Patent
Kwiatkowski et al.

(10) Patent No.: US 6,649,764 B2
(45) Date of Patent: Nov. 18, 2003

(54) STEREOSPECIFIC ENRICHMENT OF HETEROCYCLIC ENANTIOMERS

(75) Inventors: Stefan Kwiatkowski, Lexington, KY (US); Miroslaw Golinski, Lexington, KY (US); Joseph Kupper, Richmond, KY (US)

(73) Assignee: R. T. Alamo Ventures I, LLC, Beverly Hills, CA (US)

( * ) Notice: Subject to any disclaimer, the term of this patent is extended or adjusted under 35 U.S.C. 154(b) by 0 days.

(21) Appl. No.: 09/999,613

(22) Filed: Oct. 25, 2001

(65) Prior Publication Data

US 2003/0120075 A1 Jun. 26, 2003

(51) Int. Cl.⁷ .................. C07D 215/36; A61K 31/47
(52) U.S. Cl. ........................ 546/165; 514/312
(58) Field of Search ................ 546/155; 514/312

(56) References Cited

U.S. PATENT DOCUMENTS 4,302,460 A * 11/1981 Davies
5,011,931 A    4/1991  MacLean et al. ............ 546/155
5,079,264 A    1/1992  MaClean et al. ............ 514/629

FOREIGN PATENT DOCUMENTS

WO          91/02724    *   3/1991

OTHER PUBLICATIONS

Morita et al., "Synthesis and Absolute Configuration of the Enantiomers of 7–Fluoro–1–methyl–3–(methylsulfinyl)–4(1H)–quinolinone (Flosequinan)," *Chem. Pharm. Bull.*, 42(10):2157–2160 (1994).

* cited by examiner

*Primary Examiner*—D. Margaret Seaman
(74) *Attorney, Agent, or Firm*—Medlen & Carroll, LLP

(57) ABSTRACT

The present invention describes methods for the stereoselective synthesis of heterocyclic enantiomers. The methods of the present invention incorporate the stereo-preferred oxidation of quinolone thiomethyl intermediates by optically active camphor based oxaziridines to provide R(+) or S(−) quinolone methylsulfinyl derivatives.

6 Claims, 12 Drawing Sheets

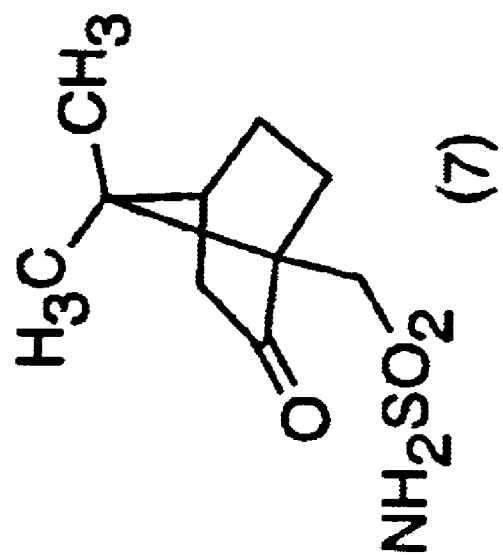
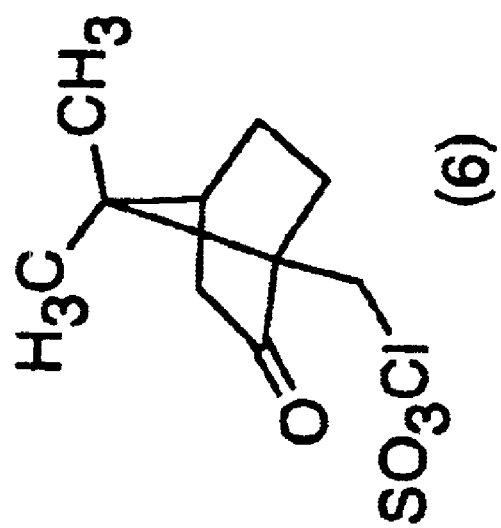
FIG. 4

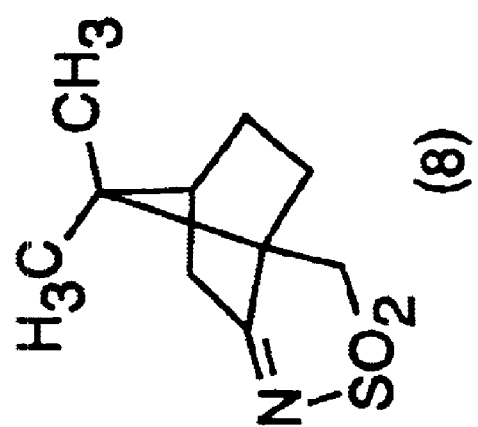
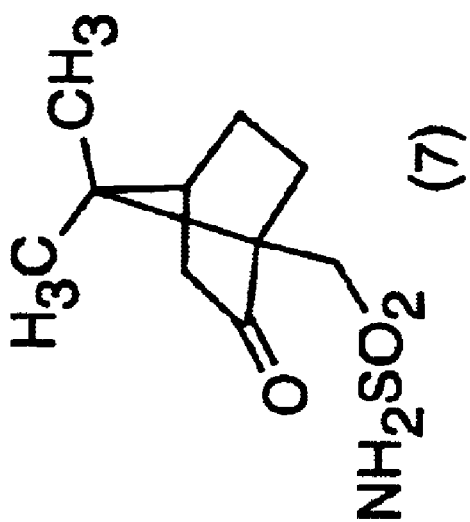
FIG. 5

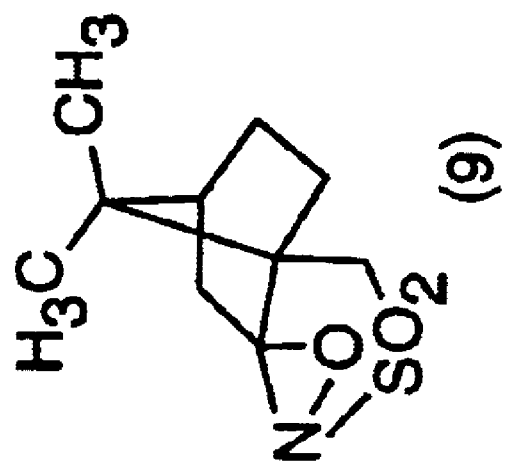
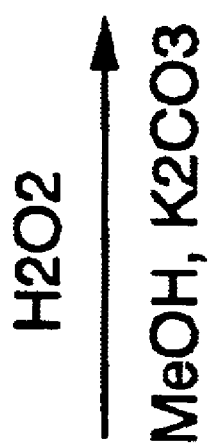
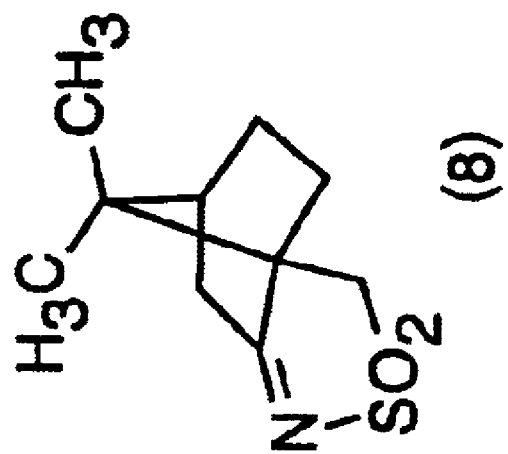
FIG. 6

CRYSTALLIZATION OF CROP I CRYSTALS FROM BATCH I
(AS DESCRIBED IN EXAMPLE 1, PARTS D & E)

CROP I CRYSTALS: 39.2g 68% e.e. R-(+)-FLOSEQUINAN
[R-(+) = 32.928g, S-(-) = 6.272g]

CROP A CRYSTALS: 17.9g 96% e.e. R-(+)-FLOSEQUINAN
[R-(+) = 17.542g, S-(-) = 0.358g]
  * FINAL PRODUCT OF BATCH 1

+

CROP B CRYSTALS: 15.329g 32% e.e. R-(+)-FLOSEQUINAN
[R-(+) = 10.09g, S-(-) = 5.23g]
  * RECYCLED TO BATCH 2

+

CROP C CRYSTALS: 5.0g 86% e.e. R-(+)-FLOSEQUINAN
[R-(+) = 4.65g, S-(-) = 0.35g]
  * ADDED TO BATCH 2, CROP I CRYSTALLIZATION

---

(0.98g OF CROP I DURING CRYSTALLIZATION

FIG. 8

STEREOSPECIFIC ENRICHMENT OF HETEROCYCLIC ENANTIOMERS

FIELD OF THE INVENTION

The present invention relates to methods for the stereoselective synthesis of heterocyclic enantiomers. The methods of the present invention incorporate the stereo-preferred oxidation of quinolone intermediates in methods for the stereoselective enrichment of the R(+) or S(−) enantiomer from a quinolone raceme mixture.

BACKGROUND

The biological activities of many pharmaceuticals, fragrances, food additives and agrochemicals are often associated with their absolute molecular configuration. Enantiomers are identical with respect to certain physical properties, such as melting and boiling points. However, enantiomers may differ in their chemical properties, particularly within biological systems. While one enantiomer may confer a desired biological function through interactions with natural binding sites, another enantiomer may not demonstrate the same function and, in some cases, may present deleterious side effects.

For example the teratogenic effects of the drug thalidomide is likely due to only one enantiomer of the drug, while the other enantiomer is believed to be a safe and useful tranquilizer devoid of teratogenic side effects. Consequently, the preparation of pharmaceutical agents as substantially pure enantiomers can offer therapeutic advantages as compared to the corresponding racemic mixture.

In view of the advantages associated with the administration of substantially pure enantiomers, chemists have explored many approaches for acquiring enantiomerically pure compounds including the resolution of the racemates using chiral stationary phases, structural modifications of naturally occurring chiral substances (as reagents for running stereospecific reactions) and asymmetric catalysis using chiral catalysts or enzymes.

Optically active catalysts or enzymes have limited application in multiple step and kilo scale processes due to their high prices. Similarly the use of chiral stationary phases, for optical resolution, is a very expensive means for kilo scale production.

What is needed, therefore, is a simplified and economical method for the stereospecific synthesis of therapeutic compounds.

SUMMARY OF THE INVENTION

The present invention relates to methods for the stereoselective synthesis of heterocyclic enantiomers. In one embodiment, the heterocyclic enantiomer is a quinolone. In another embodiment, the heterocyclic enantiomer is a substituted 4-quinolone. In a preferred embodiment, the 4-quinolone is 7-fluoro-1-methyl-3-methylsulfinyl-4-quinolone (flosequinan).

In one embodiment, the present invention describes the stereoselective oxidation of 7-fluoro-1-methyl-3-methylthio-4-quinolone as an intermediate step in the synthesis of (R)-(+) or (S)-(−) flosequinan enantiomers. In one embodiment, the methods of the present invention describe stereospecific synthesis of the (R)-(+) enantiomer of flosequinan of at least 86% optical purity. In a preferred embodiment the present invention describes stereospecific synthesis of (R)-(+)-flosequinan of at least 96% optical purity.

In one embodiment, the methods of the present invention describe the stereospecific synthesis of (S)-(−)-flosequinan of at least 86% optical purity. In a preferred embodiment the present invention describes stereospecific synthesis of (S)-(−)-flosequinan with at least 96% optical purity.

Without limiting the invention to any particular mechanism, it is believed that the R(+) and S(−) enantiomers of flosequinan differentially regulate specific phoshodiesterases as compared to racemic flosequinan. This differential effect of the R(+) or S(−) enantiomer on phosphodiesterase activity is a useful tool in therapeutic design.

In one embodiment, the present invention provides a method comprising: a) providing, i) an optically inactive, heterocyclic intermediate, and ii) an optically active camphor based reagent and; b) contacting said heterocyclic intermediate with said optically active camphor based reagent to form a mixture, c) reacting said mixture under conditions such that the (R)-(+) or (S)-(−) enantiomer of said heterocyclic intermediate is generated in excess as compared to the racemic mixture; d) recovering said R(+) or S(−) enantiomer from said mixture.

In another embodiment, the present invention further comprises, e) contacting said racemic mixture with a reducing agent under conditions such that an optically inactive heterocyclic intermediate is generated, and f) contacting said optically inactive heterocyclic intermediate with said optically active camphor based reagent under conditions such that the (R)-(+) or (S)-(−) enantiomer is generated in excess as compared to the ratio of said enantiomer in said racemic mixture.

In one embodiment, the present invention comprises a method, comprising: a) providing: i) a flosequinan racemate; ii) triphenylphosphine; and b) reacting, in a solvent, said flosequinan racemate with said triphenylphosphine under conditions such that a racemic mixture of 7-fluoro-1-methyl-3-methylthio-4-quinolone is produced. In some embodiments, said solvent is selected from the group consisting of carbon tetrachloride and a mixture of xylene and carbon tetrabromide. In some embodiments, the method further comprises the step of c) treating said racemic mixture of 7-fluoro-1-methyl-3-methylthio-4-quinolone with (1R)-(−)-(10-camphorsulfonyl)oxaziridine under conditions such that R-(+)-flosequinan is produced in enantiomeric excess.

In another embodiment, the present invention comprises a method, comprising: a) providing: i) a flosequinan racemate; ii) triphenylphosphine; and b) reacting, in a solvent, said flosequinan racemate with said triphenylphosphine under conditions such that a racemic mixture of 7-fluoro-1-methyl-3-methylthio-4-quinolone is produced, and c) treating said racemic mixture of 7-fluoro-1-methyl-3-methylthio-4-quinolone with (1S)-(+)-(10-camphorsulfonyl)oxaziridine under conditions such that S-(−)-flosequinan is produced in enantiomeric excess.

DESCRIPTION OF THE DRAWINGS

FIG. 4 presents a scheme for the synthesis of (1R)-(−)-10-camphorsulfonyl amide [i.e. compound (7)].

FIG. 5 presents a scheme for the synthesis of (+)-(camphorsulfonyl) imide [i.e. compound (8)].

FIG. 6 presents a scheme for the synthesis of (2S,8aR)-(−)-10-(camphorsulfonyl)-oxaziridine [i.e. compound (9)].

FIG. 8 presents an overview of the crystallization of (R)-(+)-flosequinan in batches with varying percentages of enantiomer excess.

DEFINITIONS

Figure 1:
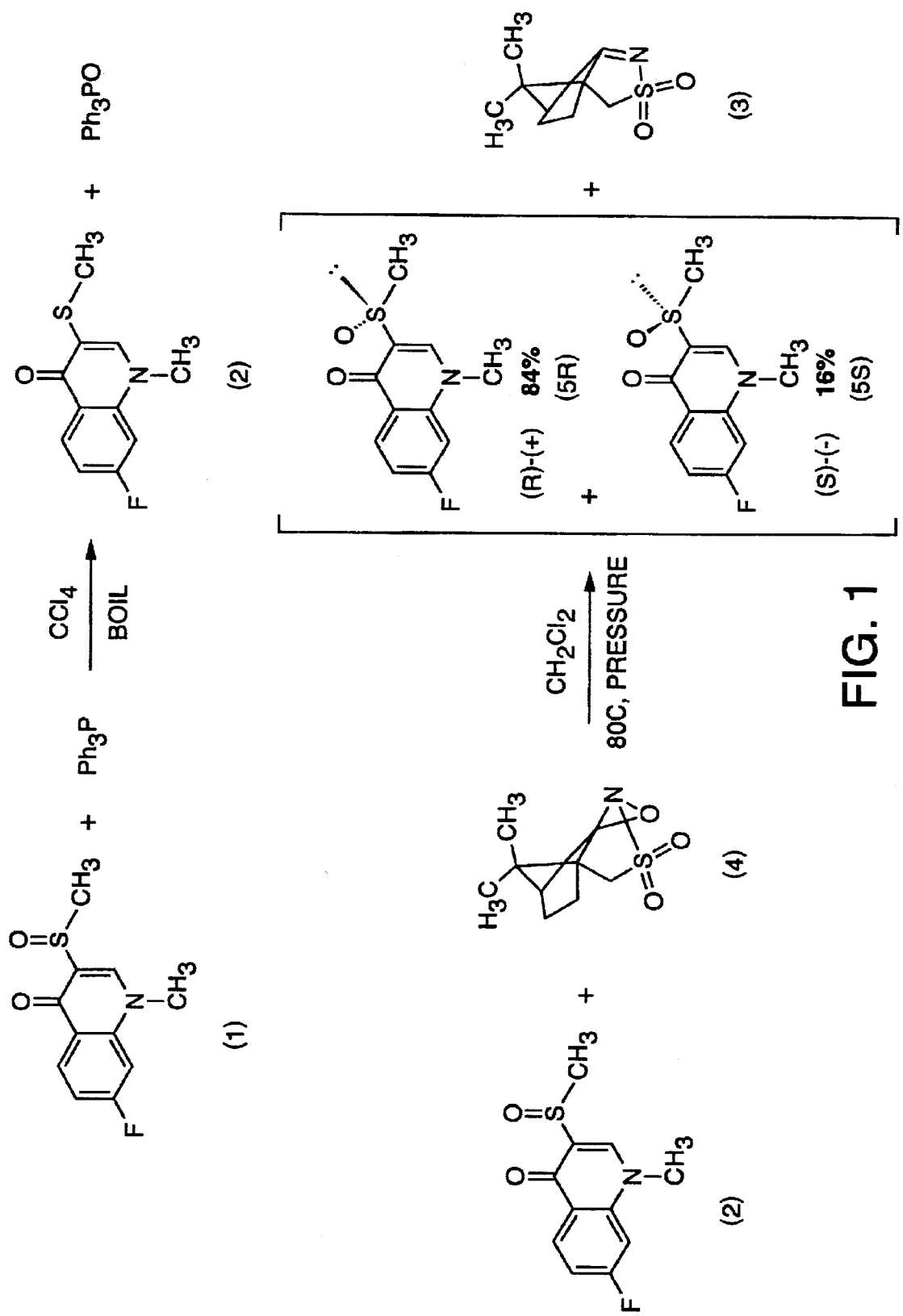
FIG. 1 presents a scheme for the reduction of racemic flosequinan (1) to 7-fluoro-1-methyl-3-methylthio-4-quinolone [i.e. compound (2)], followed by the stereopreferred oxidation of 7-fluoro-1-methyl-3-methylthio-4-quinolone (2) by (IR)-(−)-(10-camphorsulfonyl)-oxaziridine (i.e. compound 4) into a mixture of (R)-(+)-flosequinan [84%] with (S)-(−)-flosequinan [16%].

As used herein, the term "enantiomer" refers to stereoisomers of molecules that are non-superimposable mirror images of each other. Enantiomers have identical physical properties, such as melting points and boiling points, and also have identical spectroscopic properties. Enantiomers differ from each other with respect to their interaction with plane-polarized light and with respect to biological activity. As used herein, the term "stereoisomer" refers to compounds that have their atoms connected in the same order but differ in the arrangement of their atoms in space. (e.g. L-alanine and D-alanine).

As used herein, the phrase "flosequinan" refers to 7-fluoro-1-methyl-3-methylsulfinyl-4-quinolone having the chemical structure depicted below:

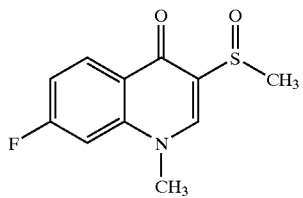

As used herein, the phrase "racemic flosequinan" or "flosequinan racemate" refers to a mixture of the two enantiomers of flosequinan. An ideal racemic mixture of the enantiomers of flosequinan refers to a 1:1 mixture of the (S)-(−)- and (R)-(+) enantiomers of flosequinan, such that the optical rotation of the (+)-enantiomer cancels out the optical rotation of the (−) enantiomer.

As used herein, the phrases "(R)-(+)-enantiomer of flosequinan" refers to (R)-(+)-7-fluoro-1-methyl-3-methylsulfinyl-4-quinolone, having the chemical structure depicted below:

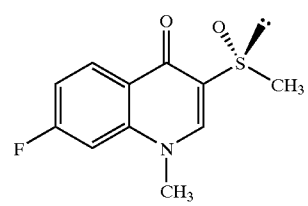

As used herein, the phrases "(S)-(−)-enantiomer of flosequinan" refers to (S)-(−)-7-fluoro-1-methyl-3-methylsulfinyl-4-quinolone, having the chemical structure depicted below:

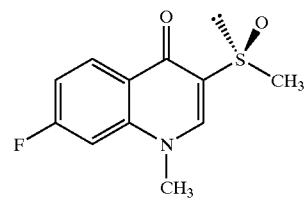

As used herein, the terms "substantially purified enantiomer" and "substantially purified enantiomer preparation" are meant to indicate a preparation (e.g. derived from non optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

As used herein, the term "racemic mixture" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

As used herein, the phrase "enantiomeric excess" or "e.e." refers to a reaction product wherein one enantiomer is produced in excess of the other and the percentage of the excess enantiomer is calculated using either (or both) of the following algorithms:

Algorithm No. 1: enantiomeric excess=(specific rotation of the reaction product/specific rotation of the pure enantiomer in excess)×100.

Algorithm No. 2: enantiomeric excess=(moles of major enantiomer−moles of other enantiomer/total moles of both enantiomers)×100.

As an example (the values in this example are offered for illustration only and do not represent data subsequently expressed in the "Experimental" section of this application), the observed rotation of a reaction product +8.52 degrees of rotation and the specific rotation of the R-configured enantiomer is reported as +15.00 degrees of rotation. The sign of the specific rotation of the reaction product indicates which enantiomer is in excess (e.g. in this example the R-configured isomer is in excess). If these values are inserted into Algorithm No. 1, the enantiomeric excess=(+8.52/+15.00)(100)=56.8% in excess of the R-isomer.

Whether expressed as a "purified enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by weight) and (or) the percent enantiomeric excess of the major enantiomer may be used to determine whether the preparation represents a purified enantiomer preparation.

As used herein, the term "optical purity" refers to the ratio of the observed optical rotation of a sample consisting of a mixture of enantiomers to the optical rotation of one pure enantiomer.

As used herein, the term "camphor based reagents" are reagents comprising a camphor moiety, as shown below:

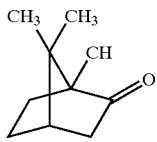

Camphor based reagents include but are not limited to the following:
(1R)-(-)-(10-Camphorsulfonyl)oxaziridine [also referred to as (-)-(2R,8aS)-10-(camphorylsulfonyl)oxaziridine]:

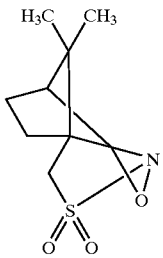

(1S)-(+)-(10-camphorsulfonyl) oxaziridine [also referred to as (+)-(2S,8aR)-10-(camphorsulfonyl)oxaziridine:

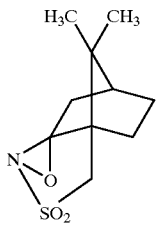

and (-)-(8,8-dichlorocamphorylsulfonyl)oxaziridine:

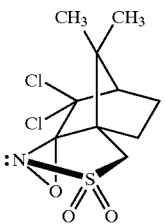

As used herein, the term "camphor based reaction product" is a compound comprising a camphor moiety, including, but not limited to, (-)-(camphorsulfonyl)imine and (+)-(camphorsulfonyl)imine.

As used herein, the phrase "pharmaceutically acceptable salts" or "a pharmaceutically acceptable salt thereof" refer to salts prepared from pharmaceutically acceptable non-toxic acids or bases including inorganic acids and bases and organic acids and bases. Since the compound of the present invention is basic, salts may be prepared from pharmaceutically acceptable non-toxic acids. Suitable pharmaceutically acceptable acid addition salts for the compound of the present invention include benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Preferred acid addition salts are the chloride and sulfate salts.

As used herein, the term "ambient temperature" is approximately 18° C. to 21° C.

As used herein, the term "overnight" is approximately 8 hours, more preferably 12 hours, more typically 17 hours, but can be up to approximately 30 hours.

As used herein, the term "heterocyclic compound" refers to a compound comprising a ring composed of atoms of more than one kind.

As used herein, the term "heterocyclic intermediate" refers to a heterocyclic compound typically produced during one of the steps of a chemical reaction and generally used in the next step of the reaction.

As used herein, "optical activity" refers to the property of certain substances to rotate plane polarized light. A compound or mixture of compounds which is "optically inactive" produces no net rotation of plane polarized light.

DETAILED DESCRIPTION OF THE INVENTION

The present invention relates to methods for the stereoselective synthesis of heterocyclic enantiomers. In one embodiment, the heterocyclic enantiomer is a quinolone. In another embodiment, the heterocyclic enantiomer is a 4-quinolone derivative. In a preferred embodiment, the quinolone is flosequinan.

In a preferred embodiment, a substantially purified (R)-(+)-enantiomer of flosequinan is prepared. It is not intended that the present invention be limited to complete separation of enantiomers, or 100% purity. It is sufficient that the preparation is enriched for one enantiomer (e.g. a 50:50 mixture becomes a 60:40 mixture). In another preferred embodiment, a substantially purified (S)-(-)-enantiomer of flosequinan is prepared. Although the present invention is not limited by a specific means of producing a substantially purified (R)-(+)- or (S)-(-)-enantiomer of flosequinan, methods of producing a racemic flosequinan, are set forth in U.S. Pat. Nos. 5,079,264 and 5,011,931 to MacLean et al., hereby incorporated by reference.

In one embodiment, racemic flosequinan is prepared according to the protocol set out in Example 4.

The present invention contemplates the stereospecific enrichment of the (R)-(+)- or (S)-(-)-enantiomer of flosequinan from racemic flosequinan. Many organic compounds, including flosequinan, exist in optically active forms (i.e., they have the ability to rotate the plane of plane-polarized light). In describing an optically active compound, the prefixes R and S are used to denote the absolute configuration of the molecule about its chiral center(s). The prefixes (+) and (-) are employed to designate the sign of rotation of plane-polarized light by the compound, with (-) meaning that the compound is levorotatory (rotates to the left). A compound prefixed with (+) is dextrorotatory (rotates to the right). For a given chemical structure, these compounds, called "stereoisomers," are identical except that they are mirror images of one another. A specific stereoisomer may also be referred to as an "enantiomer". See, Chem. Pharm. Bull. 42:2157–2160.

In one embodiment, the present invention describes the reduction of racemic flosequinan to form a thiomethyl intermediate. In one embodiment, this thiomethyl intermediate is 7-fluoro-1-methyl-3-methylthio-4-quinolone. It is not intended that the present invention be limited to a specific chemical mechanism or kinetic. Certain camphor based reagents selectively react with this thiomethyl intermediate to preferably yield either the (R)-(+) or (S)-(−) quinolone (i.e. the R(+) or the S(−) of a 4-quinolone sulfoxide derivative). That is to say, the stereochemistry of said camphor based reagents predetermines the stereochemistry of the flosequinan product. In a preferred embodiment, 7-fluoro-1-methyl-3-methylthio-4-quinolone is reacted with (1R)-(−)-(10-camphorsulfonyl)oxaziridine to yield (R)-(+)-flosequinan in enantiomeric excess. In another preferred embodiment, 7-fluoro-1-methyl-3-methylthio-4-quinolone is reacted with (1S)-(+)-(10-camphorsulfonyl)oxaziridine to yield (S)-(−)-flosequinan in enantiomeric excess.

The present invention also contemplates the formulation of an enantiomer of flosequinan (either the R-(+) or S-(−) as measured by enantiomeric excess) as a pharmaceutically acceptable salt. In addition, formulations of flosequinan enantiomers may also contain binders, fillers, carriers, preservatives, stabilizing agents, emulsifiers, buffers and excipients as, for example, pharmaceutical grades of mannitol, lactose, starch, magnesium stearate, sodium saccharin, cellulose, and magnesium carbonate.

The present invention also contemplates the recycling of a heterocyclic enantiomer [either R(+) or S(−)] (i.e. in one embodiment, the recycling of a residue flosequinan) having a enantiomeric excess less than 32% through the reduction/oxidation protocols described herein to increase the total yield of said enantiomer synthesis. Specifically, in some embodiments of the invention, the enantiomer products of the stereo-preferred oxidation reactions are typically recovered during several steps of precipitation, crystallization and filtration (to yield different batches or crops). Some steps typically produce batches or crops of the enantiomer of interest in high enantiomeric excess, while other steps typically produce batches or crops of the enantiomer of interest in lower enantiomeric excess. These low enantiomeric excess batches or crops may then be combined, for example with other batches or crops of the enantiomer of interest or with fresh racemic flosequinan (or both) and subjected to the initial reduction and stereo-preferred oxidation steps (i.e. the low % e.e. batches or crops may be recycled through the reaction steps), thereby increasing the total yield of the enantiomer of interest in high % e.e.

The present invention also provides for the isolation and recrystallization of camphor based reagents and camphor based reaction products from reaction mixtures and filtrates. The reagents which determine the stereospecific oxidation of racemic quinolone into either the R(+) or S(−) enantiomer (in term of enantiomeric excess) are not significantly consumed and/or destroyed in the reactions described by the present invention. That is to say, the present invention also provides for the efficient recycling of camphor based reagents and camphor based reaction products.

In preferred embodiments, the following examples set out methods for the stereospecific enrichment of the R(+) or S(−) enantiomer of flosequinan from racemic flosequinan according to the overall synthetic scheme outlined above.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); L (liters); ml (milliliters); $\mu$l (microliters); cm (centimeters); mm (millimeters); $\mu$m (micrometers); nm (nanometers); ° C. (degrees Centigrade); mp (melting point).

Unless otherwise stated (or in examples where specific reagents were synthesized de novo) all reagents were obtained from Aldrich, Milwaukee, Wis. (USA) and all glass equipment was obtained from Ace Glass. Louisville, Ky. (USA).

EXAMPLE 1

Figure 2A:
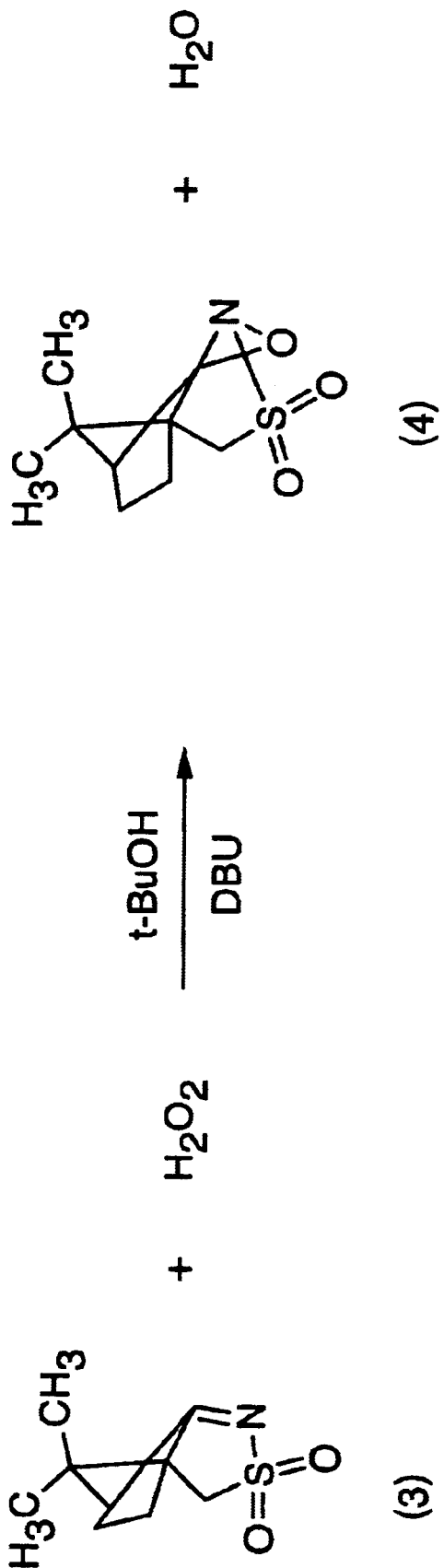
FIG. 2A presents a scheme for the oxidation of (1R)-(−)-(10-camphor sulfonyl)imine [i.e. compound (3)] to yield (1R)-(−)-(10-camphorsulfonyl)oxaziridine [i.e. compound (4)].
Figure 2B:
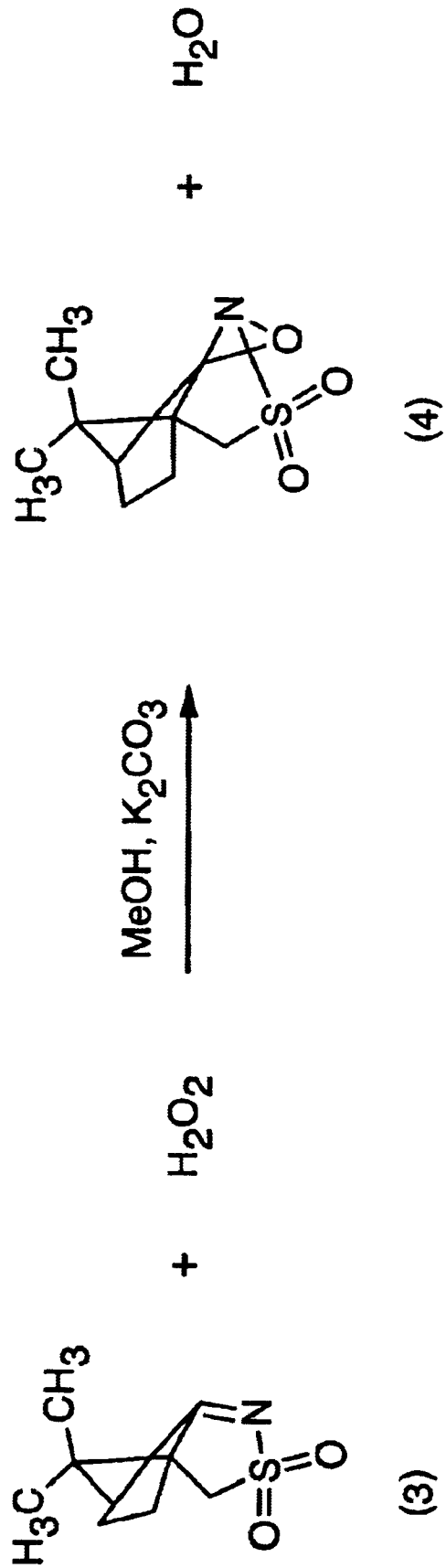
FIG. 2B presents an alternative scheme for the oxidation of (1R)-(−)-(10-camphorsulfonyl)imine [i.e. compound (3)] to yield (1R)-(−)-(10-camphorsulfonyl)oxaziridine [i.e. compound (4)].
Figure 3:
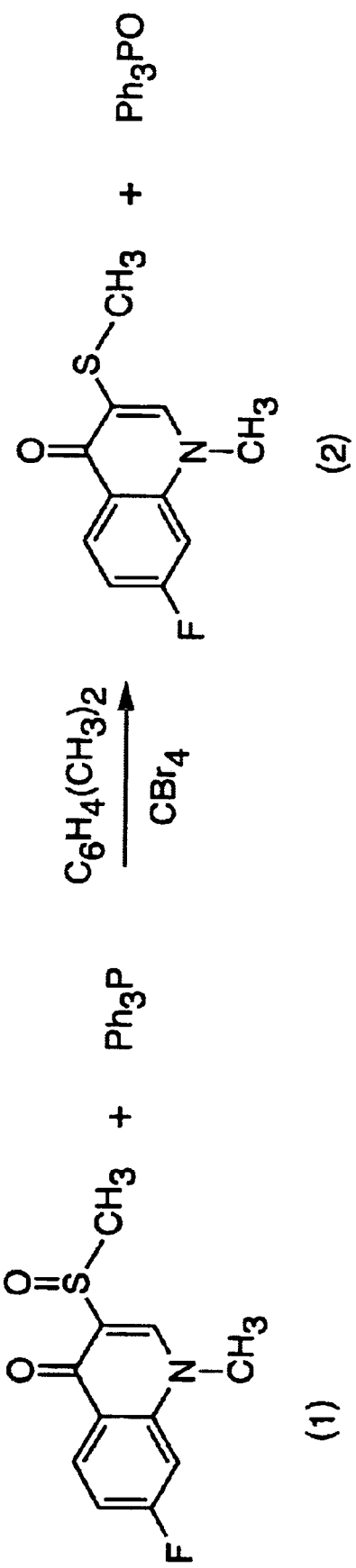
FIG. 3 presents a scheme for the reduction of flosequinan racemate [i.e. compound (1)] and synthesis of 7-fluoro-1-methyl-3-methylthio-4-quinolone [i.e. compound (2)].

In this example, the R(+) enantiomer of flosequinan was stereospecifically enriched from racemic flosequinan according to the synthetic scheme set out in FIGS. 1, 2, and 3. This overall synthetic scheme is described in more detail according to the following reactions. For the purpose of this example, all bracketed numbers [e.g. "(1)"], after the chemical name of a compound, refer to the corresponding chemical structure as designated by the same bracketed number in FIGS. 1, 2, and 3.

A. Synthesis and Purification of Camphor Based Reagents Used in the Stereoselective Enrichment of R-(+)-Flosequinan i. Synthesis of (−)-(Camphorsulfonyl)imine (3).

A 1L round-bottomed flask was equipped with a 2 inch eggshaped magnetic stirring bar, a Dean-Stark water separator, and a doublewalled reflux condenser containing at the outlet a mineral oil bubbler connected to an inert gas source. Into the flask are placed 5 g of Amberlyst 15 ion-exchange resin and 41.5 g of the crude (+)-(1S)-camphorsulfonamide in 500 ml of toluene. Amberlyst 15 is a strongly acidic ion-exchange resin. The reaction mixture was heated at reflux for 4 hr. After the reaction flask was cooled, but while it was still warm (40–50° C.), 200 ml of dichloromethane was slowly added to dissolve any camphorsulfonyl imine that crystallizes. The solution was filtered through a 150-ml sintered glass funnel of coarse porosity and the reaction flask and filter funnel were washed with an additional 75 ml of dichloromethane.

Isolation of the (−)-(camphorsulfonyl)imine was accomplished by removal of the toluene on the rotary evaporator. The resulting solid was recrystallized from absolute ethanol (750 ml) to give white crystals, 34.5–36.4 g (90–95%), mp 225–228° C.; $[\alpha]_D$ −32.7° (CHCl$_3$, c 1.9). The spectral properties of (−)-(camphorsulfonyl)imine were as follows: $^1$H NMR (CDCl$_3$) δ: 1.03 (s, 3H, CH$_3$), 1.18 (s, 3H, CH$_3$), 1.45–2.18 (m, 6H), 2.65 (m, 1H), 3.10 and 3.28 (AB quartet, 2H, CH$_2$—SO$_2$, J=14.0); $^{13}$C NMR (CDCl$_3$) δ: 19.01 (q, CH$_3$), 19.45 (q, CH$_3$, 26.64 (t), 28.44 (t), 35.92 (t), 44.64 (d), 48.00 (s), 49.46 (t), 64.52 (s), 195.52 (s), IR (CHCl$_3$)cm$^{-1}$: 3030, 2967, 1366.

ii. Hydrogen Peroxide Oxidation of (−)-(Camphorsulfonyl)imine (3) Synthesis of (1R)-(−)-(10-Camphor sulfonyl)oxaziridine (4)

FIG. 2A presents a reaction scheme for the oxidation of (−)-(camphorsulfonyl)imine (3) to yield (1R)-(−)-(10-camphorsulfonyl)oxaziridine (4) according to the following protocol. 63.9 g (0.3 mole) of (−)-(Camphorsulfonyl)imine (3) were suspended in 1.2 L of t-butyl alcohol (t-BuOH) placed in a four neck round bottom flask equipped in a mechanical stirrer, a reflux condenser, a thermometer and a dropping funnel. The reaction flask was placed in a water bath heated to approximately 50° C. and, with stirring, 4.5 g (0.03 mole) of 1,8-diazabicyclo[5,4,0]undec-7-ene (herein after referred to as "DBU") was added to the reaction mixture. This was followed by the slow addition, via a dropping funnel, of 150 ml of 30% hydrogen peroxide over a period of two hours. The reaction mixture was then stirred and heated for 2 more hours until the conversion of the imine reached 96% by mass [as confirmed by Nuclear Magnetic Resonance spectroscopy (herein after, "NMR")]. The reaction mixture was then cooled with chilled water and the excess of hydrogen peroxide was destroyed by the addition of saturated aqueous solution of sodium sulfite. The precipitated product was filtered off and washed with two aliquots of ice water (25 ml per wash). The filtrate was concentrated to the volume of 200 ml and the second crop of the product was collected on a filter, washed twice with a 5 ml portion of cold water each and combined with the first crop. After vacuum drying 64 g (93% yield) of 98+% pure (1R)-(-)-(10-camphorsulfonyl)oxaziridine (4) was obtained.

FIG. 2B presents an alternative reaction scheme for the oxidation of (-)-(camphorsulfonyl)imine (3) to yield (1R)-(-)-(10-camphorsulfonyl)oxaziridine (4). In this scheme (-)-(camphorsulfonyl)imine (3) was suspended in MeOH placed in a four neck round bottom flask equipped in a mechanical stirrer, a reflux condenser, a thermometer and a dropping funnel. The reaction flask was placed in a water bath heated to approximately 50° C. and, with stirring, $K_2CO_3$ was added to the reaction mixture. This was followed by the slow addition, via a dropping funnel, of 150 ml of 30% hydrogen peroxide over a period of two hours. The reaction mixture was then stirred and heated for 2 more hours until the conversion of the imine reaches 96% by mass [as confirmed by NMR]. The reaction mixture was then cooled with chilled water and the excess of hydrogen peroxide was destroyed by the addition of saturated aqueous solution of sodium sulfite. The precipitated product was filtered off and washed with two aliquots of ice water (25 ml per wash). The filtrate was concentrated to the volume of 200 ml and the second crop of the product was collected on a filter, washed twice with a 5 ml portion of cold water each and combined with the first crop.

B. Reduction of Flosequinan Racemate (1) and Synthesis of 7-Fluoro-1-methyl-3-methylthio-4-quinolone (2).

FIG. 1 presents a synthetic scheme for the reduction of racemic flosequinan and the subsequent synthesis of 7-fluoro-1-methyl-3-methylthio-4-quinolone (2) according to the following protocol.

90 g (0.375 mole) of solid flosequinan racemate (1), 157.5 g (0.6 mole) of triphenyl phosphine ($Ph_3P$) and 3.5 L of carbon tetrachloride ($CCl_4$) was loaded into 5 L, four neck round bottom flask (operably linked to a mechanical stirrer) wherein said flask has an inlet for nitrogen, a thermometer and a reflux condenser (with a nitrogen outlet). The reaction flask (loaded with flosequinan racemate, triphenyl phosphine, and carbon tetrachloride) was placed in an oil bath maintained at a temperature of 85–90° C. Nitrogen gas was then flowed over the reaction mixture at a rate sufficient to prevent the infiltration of air into the reaction mixture. The reaction mixture was then stirred and boiled for 2.5 hours. At this point in the reaction it was observed that all of the precipitates were dissolved and the color of the reaction mixture changed to an orange brown.

The reaction mixture was then cooled to the ambient temperature overnight and the precipitated product was collected via filtration through a sintered glass filter was then washed on the filter with two aliquots of cold carbon tetrachloride (approximately 50 ml each wash) and dried (under vacuum, of approximately 2.00 mmHg., to yield approximately 69.3 g of 7-fluoro-1-methyl-3-methylthio-4-quinolone (2).

The approximately 3.5 L filtrate (as described above) was concentrated to a final volume of 500 ml. This concentration precipitated an additional 3.3 g of the product (2), therefore the total yield of 7-Fluoro-1-methyl-3-methylthio-4-quinolone (2), was 86.7% of 99+% chemically clean compound.

C. Alternative Solvents for the Reduction of Flosequinan Racemate (1) and Synthesis of 7-Fluoro-1-methyl-3-methylthio-4-quinolone (2)

FIG. 3 projects the another scheme, using alternative solvents, for the reduction of flosequinan racemate (1) and synthesis of 7-fluoro-1-methyl-3-methylthio-4-quinolone (2). In this example, a 3.0 L round bottomed flask (with three necks) was equipped with a magnetic stirrer, a thermometer and an inlet of nitrogen. Into this flask was placed 2.0 L of anhydrous xylene [$C_6H_4(CH_3)_2$], 105 g (0.439 mole) of racemic flosequinan, 144 g (0.549 mole, 1.25 equivalent) of triphenylphosphine and 14.6 g (0.044 mole, 0.1 equivalent) of carbon tetrabromide ($CBr_4$). Nitrogen gas was then flowed over the reaction mixture at a rate sufficient to prevent the infiltration of air into the reaction mixture. The reaction mixture was stirred and heated to 100° C. for one hour. After this time the mixture was cooled to 10° C. and the product which precipitated was filtered off and washed with two 50 ml portions of xylene and subsequently dried under vacuum to yield 54.58 g of 98+% 7-fluoro-1-methyl-3-methylthio-4-quinolone (2).

The approximately 2.0 L of xylene filtrate was then concentrated (by evaporation) to the volume of 1.0 L, thereby, yielding additional 7-fluoro-1-methyl-3-methylthio-4-quinolone (2) crystals. These crystals were recrystallized from 150 g of ethanol to produce an additional 10.57 g of 98+% 7-fluoro-1-methyl-3-methylthio-4-quinolone, thereby, increasing the combined yield to a total of 65.15 g of 7-fluoro-1-methyl-3-methylthio-4-quinolone (2) which corresponded to a 66.4% yield.

1H NMR, CDC13, δ: 8.52 dd, 1H J=6.6&9.0 Hz, H-5; 7.89 s, 1H H-2; 7.15 ddd, 1H, J=2.4 & 8.1 & 9.0 Hz, H-6; 7.08 dd, 1H, J=2.1 & 10.2 Hz, H-8; 3.81 s, 3H, $NCH_3$; 2.43 s, 3H, $SCH_3$.

In another embodiment, toluene has been used as the solvent for the reduction of flosequinan with triphenylphosphine and with carbon tetrabromide.

D. Stereo-Preferred Oxidation of 7-fluoro-1-methyl-3-methylthio-4-quinolone (2). Synthesis and Separation of (R)-(+)-Flosequinan (Batch 1)

FIG. 1 also presents the stereo-preferred oxidation of 7-fluoro-1-methyl-3-methylthio-4-quinolone (2) into (R)-(+)-flosequinan (5R), as measured by enantiomeric excess, according to the following protocol.

52.2 g (0.23 mol) of 7-fluoro-1-methyl-3-methylthio-4-quinolone (2), and 375 ml of dichloromethane (DCM) were placed in a 2 L four neck round bottom flask equipped with a reflux condenser, mechanical stirrer, dropping funnel and a thermometer. The flask was then placed in a water bath maintained at 45° C. This mixture was then stirred and refluxed while a solution of 54.8 g (0.24 mole) of (1R)-(-)-(10-camphorsulfonyl)oxaziridine (4), in 450 ml of DCM, was added to the reaction mixture through a dropping funnel over the two hour period.

The mixture was then stirred and boiled for an additional 30 minutes and subsequently concentrated to dryness and then dissolved in 1.28L of boiling DCM.

This solution was then cooled at −15° C. overnight. As the solution cools, a white precipitate formed. This precipitate was collected on a scintered glass filter and washed with two 50 ml aliquots of cold DCM and vacuum dried, producing 39.2 g of 68% e.e. (R)-(+)-flosequinan (5).

At this stage in the stereospecific enrichment additional (R)-(+)-flosequinan, (−)-(camphorsulfonyl)imine (3), and unreacted (1R)-(−)(camphorylsulfonyl)oxaziridine (4) are recovered from the approximately 1.38 L of DCM filtrate (as described in the preceding paragraph). First, the approximately 1.38 L of methylene dichloride filtrate was evaporated (using a rotary evaporator) producing a yellowish solid residue.

This residue was mixed with 300 ml of acetone. The precipitate from this mixture of acetone and yellowish solid residue was filtered through a scintered glass filter and washed with two additional 10 ml aliquots of acetone. This acetone washed precipitate yielded 10.8 g of 14% e.e. (R)-(+)-flosequinan (hereinafter referred to as "Crop II crystals").

(−)-(camphorsulfonyl)imine (3) and unreacted (1R)-(−)-(Camphorylsulfonyl) oxaziridine (4) was then recovered from the approximately 320 ml of acetone filtrate. Specifically, the approximately 320 ml of acetone filtrate was evaporated (using a rotary evaporator) until a solid residue was observed. This solid residue was then dissolved in 620 ml of boiling isopropyl alcohol, and it was cooled, producing a precipitate that was collected on a sintered glass filter. This precipitate yielded a 52.4 gram mixture composed of 49.4 g of (−)-(camphorsulfonyl)imine, approximately 1.0 g of (1R)-(−)-(camphorsulfonyl)oxaziridine and approximately 2.0 g of flosequinan.

E. (R)-(+)-Flosequinan Recrystallization

The 39.2 g of 68% e.e. (R)-(+)-flosequinan (Crop I), recovered from the reaction described in section D of Example 1, was dissolved in 2.6 L of boiling water and left at ambient temperature overnight for crystallization. The long needle like colorless crystals were filtered off and washed with two 20 ml portions of water yielding, after drying, 17.9 g of 96% e.e. (R)-(+)-flosequinan representing 52.3% of (R)-(+)-enantiomer recovery. The filtrate was cooled in an ice water bath for four hours with occasional stirring and the precipitate which formed was filtered off and dried, affording 15.3 g of low enantiomeric purity of 31.7% e.e. (R)-(+)-flosequinan. The filtrate from this filtration was also evaporated to dryness and the solid product dried to afford an additional 5.0 g of 86% e.e. (R)-(+)-flosequinan.

Therefore, the stereospecific enrichment outlined in sections "D" and "E" of Example 1 yielded, overall, 39.2 g of 68% e.e. (R)-(+)-flosequinan (Crop I) wherein Crop I comprises three batches of (R)-(+)-flosequinan having discrete percentages of enantiomeric excess: i) 17.9 g of 96% e.e. (R)-(+)-flosequinan (Crop A), ii) 15.3 g of 31.7% e.e. (R)-(+)-flosequinan (Crop B) and iii) 5.0 g of 86% e.e. (R)-(+)-flosequinan (Crop C) [with 0.98 g of Crop I material lost during crystallization]. An overview of the crystallization of these three batches of (R)-(+)-flosequinan is projected in FIG. 8.

F. Recycling of Lower Purity (R)-(+)-Flosequinan 15.3 g of (R)-(+)-flosequinan of less than 32% e.e. described in section "E" of Example 1 was combined with 10.8 g of Crop II crystals, as described in section "D" of Example 1, and 32.3 g of fresh racemic flosequinan. This mixture was reacted according to the reduction reaction set out in section "B" of Example 1. As a result, 52.1 g of 7-fluoro-1-methyl-3-methylthio-4-quinolone were obtained. This material was used in the preparation of a subsequent batch (e.g. Batch II) of (R)-(+)-flosequinan.

G. Recycling of (−)-(Camphorsulfonyl)imine 52.4 g of the (−)-(camphorsulfonyl)imine described in section "D" of Example 1 was oxidized with hydrogen peroxide following the procedure given in section "A" of Example 1. As a result, 49.6 g of pure (1R)-(−)-(10-camphorsulfonyl)oxaziridine was obtained. This material was mixed with 5.2 g of oxaziridine described in section "A" and used as a substrate in the preparation subsequent batches of (R)-(+)-flosequinan.

H. Overview of Scheme, with Materials and Yields, for Multiple Batch Processing Based on Steps Example 1 (Section A-G).

Figure 9A:
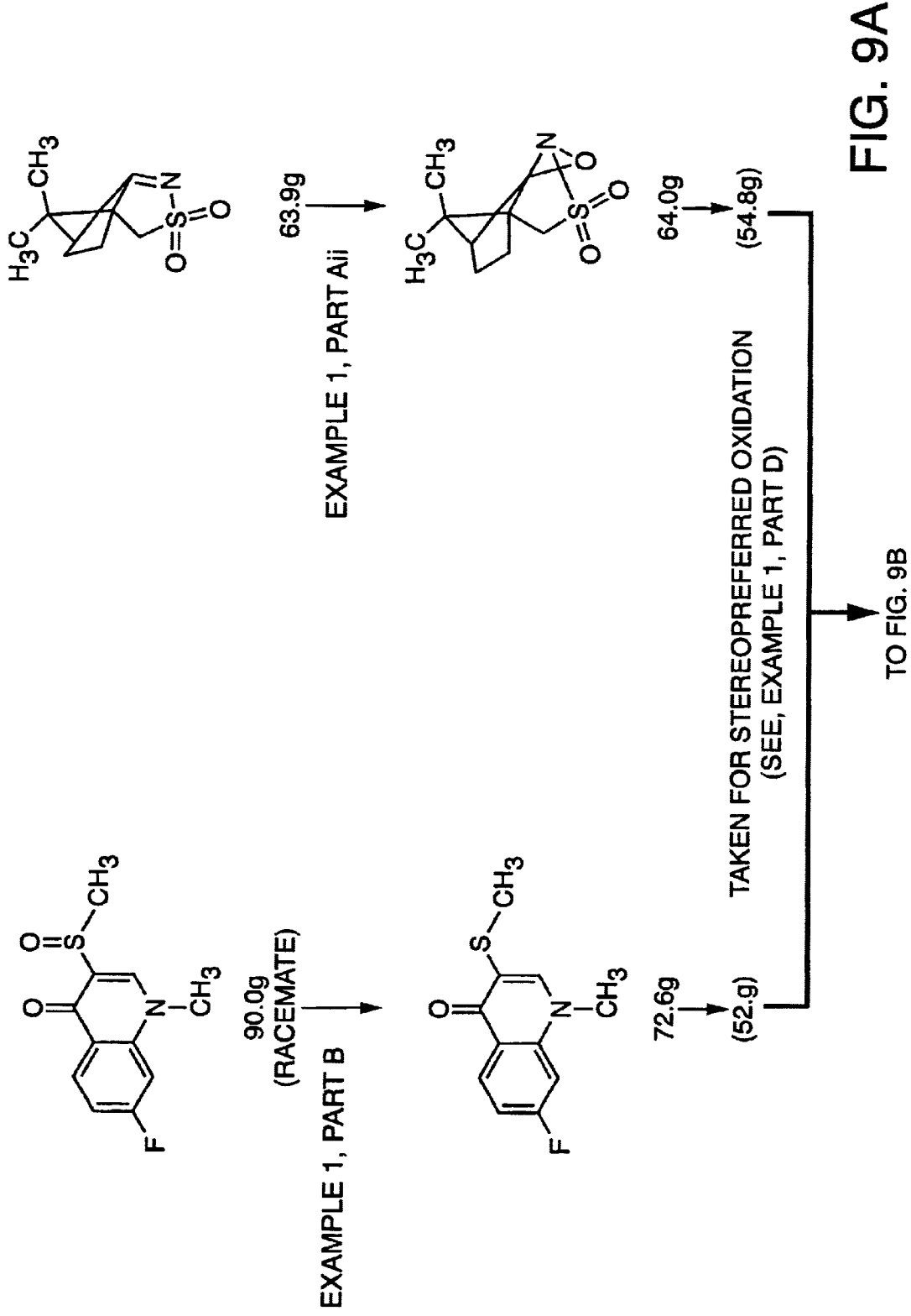
FIGS. 9A, 9B, and 9C sets out a scheme projecting an overview of the processing of batches, with varying percentages of enantiomer excess, of (R)-(+)-flosequinan.
Figure 9B:
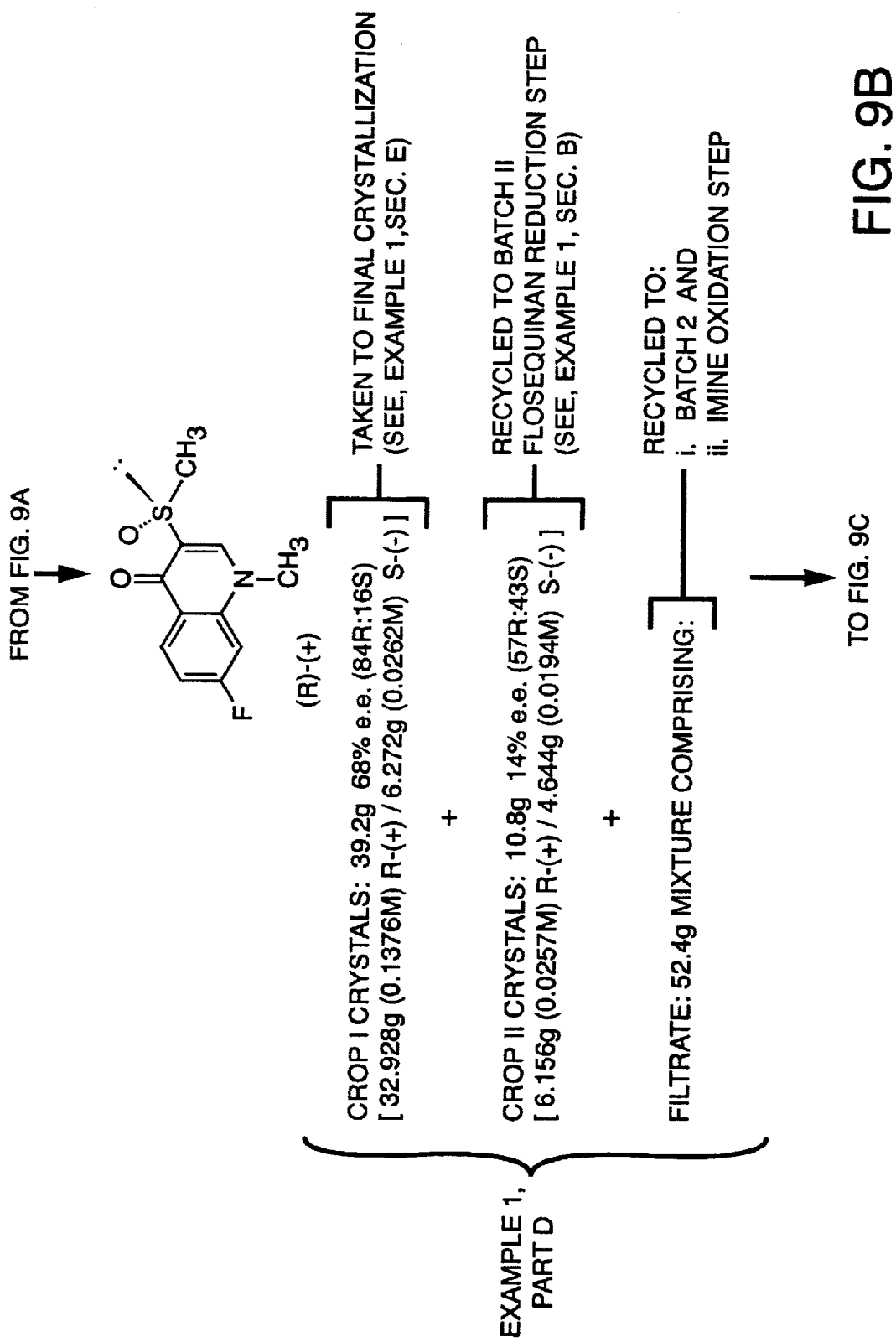
Figure 9C:
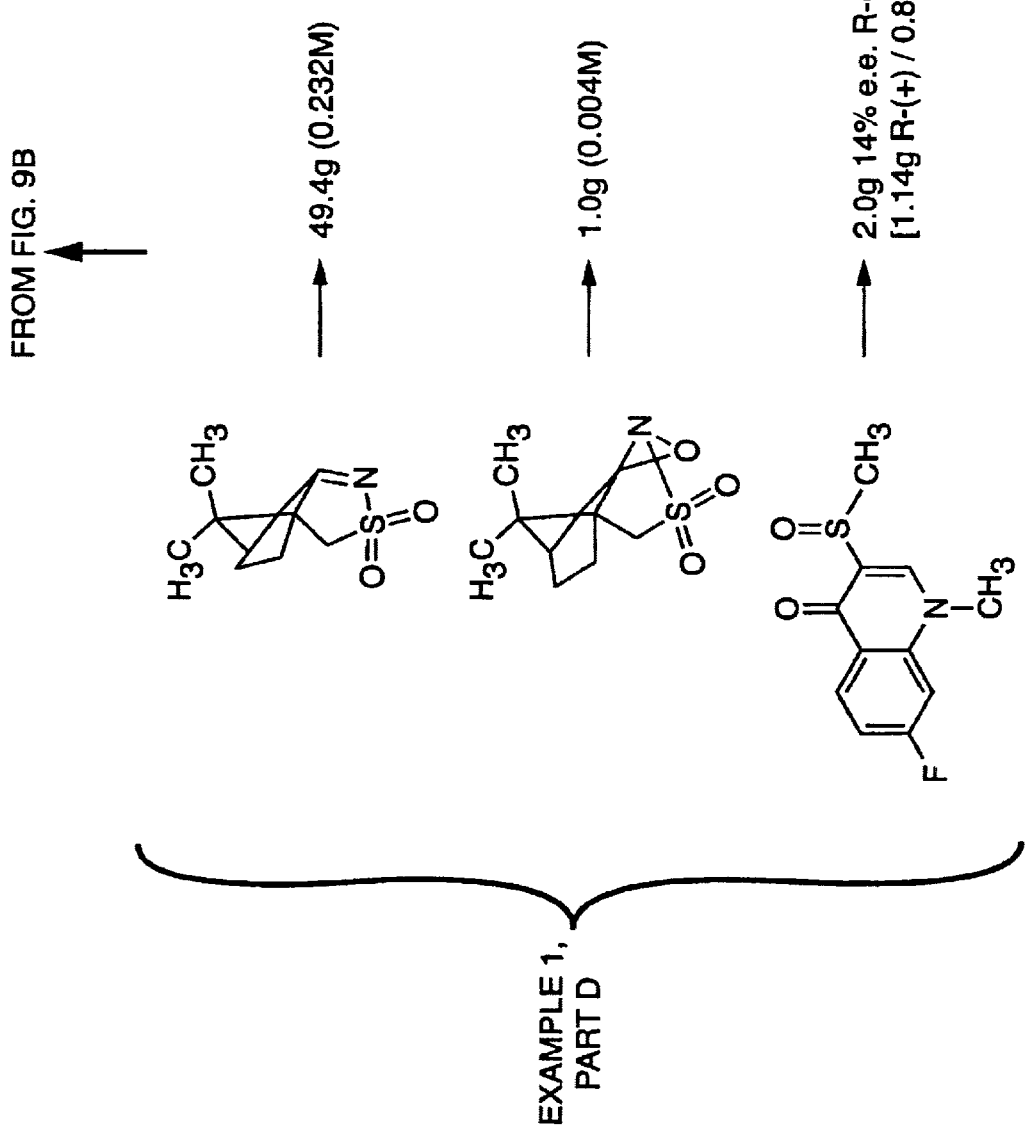

FIGS. 9A, 9B, 9C sets out a scheme projecting an overview for the processing of R-(+)-flosequinan crops with varying percentages of enantiomeric excess. More specifically, the recycling of selected crops of R-(+)-flosequinan (generated in Example 1, part E) is highlighted.

EXAMPLE 2

In this example, the S(−) enantiomer of flosequinan was stereospecifically enriched from racemic flosequinan according to the synthetic scheme set out in FIGS. 4–7. This overall synthetic scheme is described in more detail according to the following reactions. For the purpose of this example, all bracketed numbers [e.g. "(1)"], after the chemical name of a compound, refer to the corresponding chemical structure as designated by the same bracketed number in FIGS. 1–7.

A. Synthesis of (1R)-(−)-10-camphorsulfonyl Amide (2)

FIG. 4 presents the synthesis of (1R)-(−)-10-camphorsulfonyl amide according to the following protocol. 500 ml of 28% ammonium hydroxide was placed in a 2 L round bottom flask equipped with a dropping funnel, thermometer and magnetic stirring bar. The flask was placed in an ice-water cooling bath, and when the temperature in the flask dropped below +6.0° C. the addition of a solution of 50.0 g (0.2 mole) of (1R)-(−)-10-camphorsulfonyl chloride (6) in 200 ml of DCM was started. During the addition of DCM, over the course of 45 minutes, the temperature of the mixture did not exceed +6.0° C. After all of the DCM was introduced, the cooling bath was removed and the mixture was stirred at ambient temperature for an additional 30 minutes.

The reaction mixture was then transferred into a separatory funnel and the lower DCM layer was collected, while the upper aqueous layer was extracted with two 100 ml portions of DCM.

Both extracts and the DCM layer were combined, dried over anhydrous sodium sulphate, filtered, concentrated and vacuum dried to yield 45.36 g (98.3% yield) of white crystalline (1R)-(−)-10-camphorsulfonyl amide (7) which was used in Step B, of this example, without further purification.

B. Synthesis of (+)-(camphorsulfonyl) Imide (8)

FIG. 5 presents the synthesis of synthesis of (+)-(camphorsulfonyl) imide (8) according to the following protocol. 1.1 L of toluene, 90.72 g (0.392 mole) of (1R)-(−)-10-camphorsulfonyl amide (7) and 11 g of Amberlyst 15 ($H^+$ ion-exchange resin), were placed in a 2 L boiling flask equipped with a magnetic stirring bar and Dean-Stark water separator. The mixture was refluxed until water condensate was formed (after about 4 hours of continuous boiling). The mixture was then cooled to 50° C. At this time 200 ml of DCM was added to prevent precipitation.

The solution was filtered through a course sintered glass filter and the flask and filter were washed with an additional 100 ml of DCM.

The filtrate was concentrated to dryness and the resulting solid material was crystallized from 1250 ml of isopropyl alcohol to give 82.0 g (98% yield by mass) of white crystalline (+)-(camphorsulfonyl) imine (3) having a melting point of 257.0–227.5° C.

C. Synthesis of (2S,8aR)-(+)-10-(camphorsulfonyl)-oxaziridine (9)

FIG. 6 presents the synthesis of (2S,8aR)-(+)-10-(camphorsulfonyl)-oxaziridine (9) according to the following protocol. A magnetic stirring bar, 82.0 g (0.384 mole) of (+)-(camphorsulfonyl) imine (8), 750 ml of methyl alcohol and 53.21 g of potassium carbonate were placed into a 2 L round bottom flask equipped with a reflux condenser, a thermometer and a dropping funnel. This loaded apparatus was then placed in a water bath maintained at approximately 20° C. Stirring was started and 44.4 ml (52.4 g, 0.77 mole) of 50% hydrogen peroxide ($H_2O_2$) was added slowly, under conditions such that the reaction mixture did not exceed 30° C. It took one hour to add $H_2O_2$ such that 96.5% of imine (8) was converted into compound (9). The reaction mixture was diluted with 500 ml of water and 500 ml of DCM. The bottom, organic layer was collected while the upper, aqueous layer was extracted with two 100 ml portions of DCM. The DCM solutions were combined and concentrated to dryness using a rotary evaporator to yield 74.0 g (80.5% yield by mass) of the (2S, 8aR)-(+)-10(camphorsulfonyl) oxaziridine (9) which was contaminated with 2% of starting imine. This (2S, 8aR)-(+)-10(camphorsulfonyl) oxaziridine (9) was used in Step D without further purification.

D. Synthesis of (S)-(−)-flosequinan (6)

Figure 7:
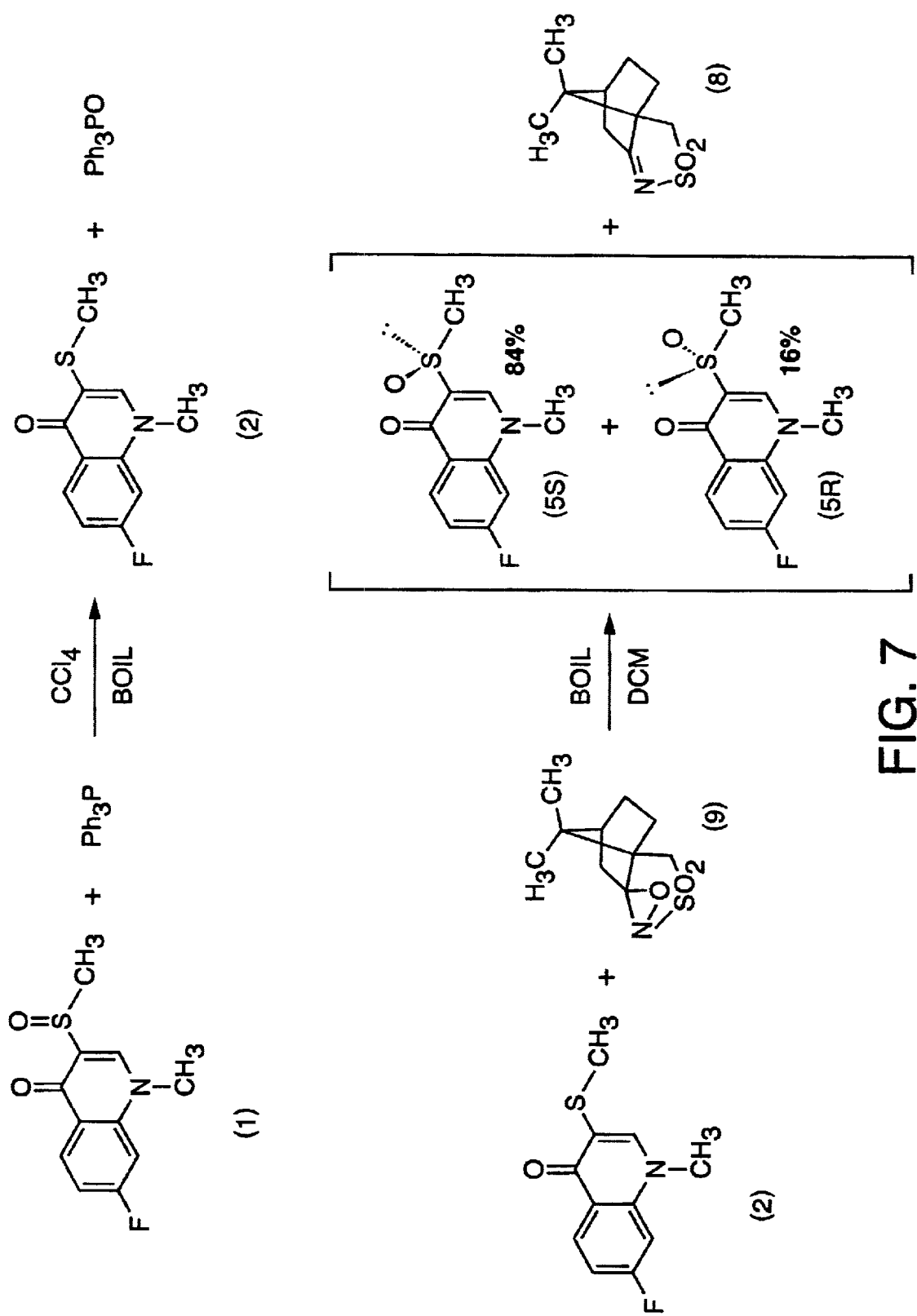
FIG. 7 presents a scheme for the reduction of racemic flosequinan [i.e. compound (1)] and the subsequent synthesis of 7-fluoro-1-methyl-3-methylthio-4-quinolone [i.e. compound (2)], followed by the stereo-preferred oxidation of 7-fluoro-1-methyl-3-methylthio-4-quinolone [i.e. compound (2)] into a mixture of (S)-(−)-flosequinan [84%] with (R)-(+)-flosequinan [16%].

FIG. 7 presents the synthesis of (S)-(−)-flosequinan (6) according to the following protocol. A magnetic stirring bar, 30.075 g (0.1347 mole) of 7-fluoro-1-methyl-3 methylthio-4-quinolone (2) and 325 mL of DCM were placed into a 1 L round bottom flask equipped with a reflux condenser and a dropping funnel. This loaded apparatus was then placed in an oil heating bath maintained at approximately 50° C. When the reaction mixture started to boil, a solution of 32.781 g (0.14 mole) of (2S, 8aR)-(+)-10-(camphorsulfonyl) oxaziridine (9) dissolved in 225 ml of DCM was added over one hour. This mixture was boiled for 1.5 hours, after which time the stirring and heating was stopped and the flask was placed in a refrigerator maintained at approximately −7.0° C. overnight.

The precipitate that formed was filtered and vacuum dried to yield 21.824 g (67.7% yield by mass) flosequinan, comprising (5S) and (5R). This flosequinan was crystallized in order to separate out the (S)-(−)-enantiomer. See, Step E of Example 2. The filtrate was concentrated to dryness and the solid residue was crystallized from 900 ml of ethyl alcohol to yield 27.365 g (91.6% regeneration) of (+)-(camphor sulfonyl) imine (8).

E. Separation of (S)-(−) Flosequinan (5S)

21.824 g of crystallized flosequinan from Step D was dissolved in 1450 ml of boiling water and left at ambient temperature overnight, without stirring for crystallization. The crystals formed were filtered off and vacuum dried to yield 13.427 g of 68% e.e. (S)-(−)-flosequinan. The filtrate was cooled, with stirring, in an ice-water bath for four hours. At the end of four hours of cooling, 5.577 g of 5% e.e. crystalline (S)-(−)-flosequinan was recovered. The filtrate was concentrated and vacuum dried to yield 2.297 g of 65.4% e.e. (S)-(−)-flosequinan.

The crystals with high concentration of (S)-(−)-flosequinan were combined and recrystallized from 740 ml of boiling water.

The solution was left overnight, at ambient temperature, without stirring. The precipitate which formed was subsequently filtered off and vacuum dried to yield 6.873 g of 99% e.e. (S)-(−)-flosequinan. The filtrate was cooled, with stirring, in an ice-water for four hours. The resulting precipitate was filtered and vacuum dried to yield 7.864 g of 37.1% e.e. (S)-(−)-flosequinan. The filtrate was concentrated to dryness to yield 0.964 g of 92.2% e.e. (S)-(−)-flosequinan. The fractions with high e.e. values were combined to yield 7.837 g (25.3% yield) of 98% e.e. (S)-(−)flosequinan (5 S).

EXAMPLE 3

In this example, racemic flosequinan, (R)-(+)-flosequinan, and (S)-(−)-flosequinan were subjected to biochemical enzyme assays to determine their respective percent inhibition of a variety of phosphodiesterases (PDE1–PDE6). The (R)-(+)-flosequinan and (S)-(−)-flosequinan used in this example was resolved by high-performance liquid chromatography (HPLC) as follows. A 5.0 g sample of a racemic mixture of flosequinan was resolved over a 10 cm ID×50 cm L CHIRALCEL OD HPLC column (Chiral Technologies, Exton, Pa.) at 25° C. and with a flow rate of 1.0 ml/minute such that the column pressure was 37 bar. The mobile phase employed was 100% methanol and the detection of the mixture was performed at 270 nm. The (−) enantiomer had a retention time of 3.13 minutes, while the (+) enantiomer had a retention time of 4.40 minutes. A total of 2.1 g of the (−) enantiomer having an optical purity greater than 99% was produced. A total of 2.3 g of the (+) enantiomer having an optical purity greater than 99% was produced.

The reaction conditions for each PDE assay were as follows.

PDE1: PDE1 partially purified from bovine heart was used. A racemic mixture of flosequinan, and each enantiomer of flosequinan, all at a molar concentration of 100 $\mu$M, were independently incubated with 13 $\mu$g PDE1 enzyme, 1.0 $\mu$M [$^3$H]cAMP and Cal$_2$/calmodulin in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE2: PDE2 partially purified from human platelets was used. A racemic mixture of flosequinan, and each enantiomer of flosequinan, all at a molar concentration of 100 $\mu$M, were independently incubated with 23 $\mu$g PDE2 enzyme, 25 $\mu$M cAMP containing 0.05 $\mu$M [$^3$H]cAMP in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE3: PDE3 partially purified from human platelets was used. A racemic mixture of flosequinan, and each enantiomer of flosequinan, all at a molar concentration of 100 $\mu$M, were independently incubated with 13 $\mu$g PDE3 enzyme and 1 $\mu$M cAMP containing 0.01 $\mu$M [$^3$H]cAMP in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [³H]adenosine in the aqueous phase was quantitated by scintillation counting.

PDE4: PDE4 partially purified from human U-937 pronocytic cells was used. A racemic mixture of flosequinan, and each enantiomer of flosequinan, all at a molar concentration of 100 μM, were independently incubated with 20 μg PDE4 enzyme and 1 μM cAMP containing 0.01 μM [³H]cAMP in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [³H]adenosine in the aqueous phase was quantitated by scintillation counting.

PDE5: PDE5 partially purified from human platelets was used. A racemic mixture of flosequinan, and each enantiomer of flosequinan, all at a molar concentration of 100 μM, were independently incubated with 120 μg PDE5 enzyme and 1 μM cGMP containing 0.01 μM [³H]cGMP in Tris buffer pH 7.5 for 20 minutes at 30° C. The reaction was terminated by boiling for 2 minutes, and the resulting GMP was converted to guanosine by addition of 10 mg/ml snake venom nucleotidase and further incubation at 30° C. for 10 minutes. Unhydrolyzed cGMP was bound to AGI-X2 resin, and the remaining [³H]guanosine in the aqueous phase was quantitated by scintillation counting.

PDE6: PDE6 partially purified from bovine retinal rod and activated by trypsin was used. A racemic mixture of flosequinan, and each enantiomer of flosequinan, all at a molar concentration of 100 μM, were independently incubated with 0.2 μg/ml active PDE6 and 100 μM cGMP containing 0.1 μM [³H]cGMP in Tris buffer pH 7.5 for 20 minutes at 30° C. Each reaction was terminated by boiling for 2 minutes. The resulting GMP was converted to guanosine by addition of 10 mg/ml snake venom nucleotidase, and further incubated at 30° C. for 10 minutes. Unhydrolyzed cGMP was bound to AGI-X2 resin, and [³H]guanosine remaining in the aqueous phase was quantitated by scintillation counting.

The results of the above PDE assays are presented in Table 1. The results indicate that the (+) enantiomer of flosequinan demonstrated more PDE1 and PDE3 inhibitory activity when compared with the (−) enantiomer of flosequinan. These empirical results could not be predicted.

TABLE 1

| Target Phosphodiesterase | % Inhibition w/ 100 μM racemic mixture of flosequinan | % Inihibition w/ 100 μM (+)- flosequinan | % Inhibition w/ 100 μM (−)- flosequinan |
|---|---|---|---|
| PDE1 | 31 | 28 | 11 |
| PDE2 | 18 | 18 | 13 |
| PDE3 | 26 | 32 | 5 |
| PDE4 | 24 | 6 | 1 |
| PDE5 | 11 | 17 | 10 |
| PDE6 | 21 | 22 | 21 |

EXAMPLE 4

In this example racemic flosequinan is prepared according to the following protocol.

A. Preparation of Racemic Flosequinan i. Step I

In a clean and dry 12 liter glass reactor equipped with a back suction trap plus a NaOH (25%) trap at the outlet and a back suction trap in the inlet, 3.840 liters of toluene were charged and cooled to −45° C. using a dry ice-acetone bath. Using appropriate safety precautions, 832 g of phosgene were then passed through the cold toluene while stirring to prepare a 20% (wt/wt) solution. The addition of the phosgene took approximately 3.5 hours.

Separately, into a clean and dry 22 liter glass reactor equipped with the above-described types of back suction traps, 399 g of starting material (formula I):

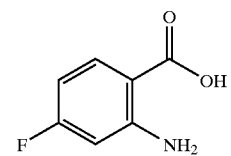

I was added with stirring to 4.37 liters of deionized water. A separate 6.8% solution of sodium carbonate in water was also prepared by adding 297 g of sodium carbonate to 4.37 liters of deionized water. Using a clean addition funnel, the sodium carbonate solution was then slowly added with stirring to the suspension of the starting material, to create a brown-colored solution.

In preparation for the reaction step, the phosgene solution was warmed from −45° C. to −15° C. and the mixture of the starting material and the sodium carbonate 110 was cooled to 10° C. The phosgene solution was then added over approximately 1.5 hours with stirring to the brown solution. The reaction mixture was stirred overnight allowing the desired intermediate-A (formula II):

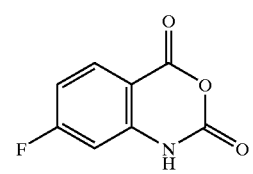

II to precipitate out. A sample was removed for NMR assessment and the precipitate was filtered on a 4 liter sintered glass funnel. The filtrate was washed with 2×500 ml aliquots of cold deionized water and dried under a vacuum at approximately 50° C. for 16 hours.

A 93.4% lot yield of 435 g of intermediate-A (formula II) was obtained. This procedure was repeated three more times, starting with approximately 400 g of starting material each time. Lot yields of 448 g (94.5%), 449 g (95.9%), and 459 g (96.8%) were obtained.

ii. Step II

In a 22L oven dried glass reactor equipped with a reflex condenser, addition funnel and temperature recorder, 11.40 liters of anhydrous tetrahydrofuran (THF) were added under nitrogen. To this reactor were also added 409 g of 60% sodium hydride in oil. Eight approximately equal portions of intermediate-A (formula II) were then added to the reactor, totaling 883 g altogether. As this reaction is exothermic, care was taken to avoid excessive heat and bubbling. Final temperature was 40° C., with a maximum observed temperature of 41° C. The reaction mixture was stirred until hydrogen gas evolution ceased.

To the reaction mixture was then slowly added 575 ml (766.4 g) of dimethyl sulfate, keeping the temperature below 50° C. Upon completion, the reaction mixture was stirred at 50° C. for 3 hours with the reflux condenser on. A sample was removed for NMR assessment, and the heat was turned off before stirring overnight.

In the morning, the stirring was stopped and the clear liquid on top was siphoned off. This liquid was filtered using a 2–3 inch thick Celite pad in a 2_liter sintered glass funnel. The residue cake was kept covered to minimize contact with atmospheric moisture. The residue was collected and washed with 4 aliquots of anhydrous THF. The filtrate and the washings were evaporated to dryness using a rotary evaporator and the residue obtained was dried under vacuum at approximately 36–38° C. overnight. A sample was removed for NMR assessment of the amount of unreacted dimethyl sulfate present. The dried residue was then added to 1600 ml of a 1:3 toluene:hexane mixture and vigorously stirred. This mixture was then filtered and washed with 2×700 ml washings of 1:3 toluene:hexane mixture. A reference sample was removed for NMR assessment and the residue was dried at 51–50° C. under vacuum for 36 hours.

This batch yielded 871 g of intermediate-B (formula III):

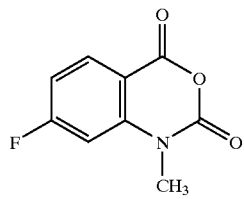

III for a lot yield of 91.6%. Another 907.1 g of intermediate-A was subjected to the procedure of step_II, in which the amounts of reactants and solvents was proportionately adjusted with a yield of 850 g (87%).

iii. Step III

In an oven dried 12 liter glass reactor equipped with a stirrer, temperature recorder and addition funnel, 2550 ml of anhydrous toluene was added-under nitrogen. Then 236 g of 60% sodium hydride in oil was added, all at room temperature. The reaction mixture was heated with continuous stirring to 75° C. using a heating mantel. Then 1.59 liters of anhydrous dimethyl sulfoxide (DMSO) were added slowly and carefully over 45 minutes taking care to avoid excessive bubbling. The reaction mixture was stirred for one hour at 70–72° C. until clear and hydrogen gas evolution ceased. The heating mantel was turned off and a water bath was used to cool the reaction mixture to 30° C.

To this mixture, 538.2 g of dry intermediate-B (formula III) was added slowly in portions, keeping the temperature no higher than 35° C. Then 1.9 liters of anhydrous DMSO was added, again keeping the temperature no higher than 35° C. The reaction mixture was stirred under nitrogen for one hour, allowing the mixture to cool to 26°. The reaction mixture was then quenched slowly and carefully with 320 ml of methanol. The resulting suspension was then added slowly and with vigorous stirring to a 22 liter reaction vessel containing 12.760 liters of diethyl ether.

After stirring was stopped, the upper ether layer was siphoned off and the brown oil lower layer was washed with 520 ml of fresh ether. The oily yellow residue was triturated with 2600 ml of deionized water until a yellow precipitate formed. This precipitate was filtered using a 2 liter sintered glass funnel and the solid residue was washed with three aliquots of 130 ml cold deionized water. A reference sample was taken to assess the residue. The residue was dried under vacuum at 50–53° C. for 23 hours.

This procedure produced 243 g of intermediate C (formula IV):

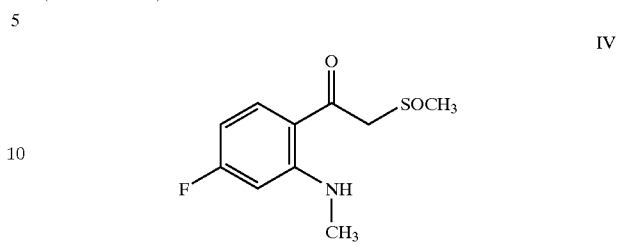

IV which represents a 38.4% yield. Two other batches of intermediate-B were treated according to this Step III procedure, with proportionate adjustments to the amounts of reactants and solvents. The first additional batch of 538.2 g intermediate-B produced a 192 g (30.4%) yield, and the second additional batch of 87.38 g of intermediate-B produced a yield of 42 g (40.9%).

iv. Step IV

In a 12 liter oven dry glass reactor equipped with a stirrer, temperature recorder and addition funnel which has been dried by nitrogen flow for 30 minutes the following chemicals were charged: 7.990 liters of triethyl orthoformate; 696 g of intermediate-C; 324 ml of piperdine; and 296 ml of acetic acid. The reaction mixture was heated under nitrogen to reflux at approximately 105° C. for 2 hours. A sample was removed to assess the progress of the reaction step by NMR.

Using a water bath, the reaction mixture was then cooled to room temperature and stirred for 30 minutes. The final product precipitated out and was collected by filtration on a 4 liter sintered glass funnel. The residue was washed with 3×700 ml aliquots of diethyl ether, and a sample was removed for NMR assessment. The residue was dried under vacuum at 50–51° C. for 17 hours. A sample of the dried flosequinan product (formula V):

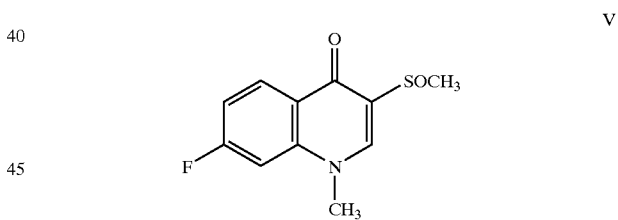

V was removed for NMR assessment. 547 g (75.3%) yield of flosequinan was obtained (an additional 47 g of product was scraped from the bottom of the sintered glass filter but was not included in this total yield calculation).

All publications and patents mentioned in the above specification are herein incorporated by reference. Various modifications and variations of the described invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A method of synthesizing 7-fluoro-1-methyl-3-methylthio-4-quinolone, comprising:

a) providing: i) a racemic mixture of 7-fluoro-1-methyl-3-methylsulfinyl-4-quinolone; ii) triphenylphosphine; and b) reacting, in a solvent, said racemic mixture of 7-fluoro-1-methyl-3-methylsulfinyl-4-quinolone with said triphenylphosphine under conditions such that 7-fluoro-1-methyl-3-methylthio-4-quinolone is produced.

2. The method of claim 1, wherein said solvent is selected from the group consisting of carbon tetrachloride and a mixture of xylene and carbon tetrabromide.

3. A method of synthesizing (S)-(−)-7-fluoro-1-methyl-3-methylsulfinyl-4-quinolone in enantiomeric excess, comprising:

a) providing: i) a racemic mixture of 7-fluoro-1-methyl-3-methylsulfinyl-4-quinolone; ii) triphenylphosphine;

b) reacting, in a solvent, said racemic mixture of 7-fluoro-1-methyl-3-methylsulfinyl-4-quinolone with said triphenylphosphine under conditions such that 7-fluoro-1-methyl-3-methylthio-4-quinolone is produced; and c) treating said 7-fluoro-1-methyl-3-methylthio-4-quinolone with (1S)-(+)-(10-camphorsulfonyl)oxaziridine under conditions such that (S)-(−)-7-fluoro-1-methyl-3-methylsulfinyl-4-quinolone is produced in enantiomeric excess.

4. The method of claim 3, wherein said solvent is selected from the group consisting of carbon tetrachloride and a mixture of xylene and carbon tetrabromide.

5. A method of synthesizing (R)-(+)-7-fluoro-1-methyl-3-methylsulfinyl-4-quinolone in enantiomeric excess, comprising:

a) providing: i) a racemic mixture of 7-fluoro-1-methyl-3-methylsulfinyl-4-quinolone; ii) triphenylphosphine;

b) reacting, in a solvent, said racemic mixture of 7-fluoro-1-methyl-3-methylsulfinyl-4-quinolone with said triphenylphosphine under conditions such that 7-fluoro-1-methyl-3-methylthio-4-quinolone is produced; and c) treating said 7-fluoro-1-methyl-3-methylthio-4-quinolone with (1R)-(−)-(10-camphorsulfonyl)oxaziridine under conditions such that (R)-(±)-7-fluoro-1-methyl-3-methylsulfinyl-4-quinolone is produced in enantiomeric excess.

6. The method of claim 5, wherein said solvent is selected from the group consisting of carbon tetrachloride and a mixture of xylene and carbon tetrabromide.

* * * * *